(12) United States Patent
Boulis

(10) Patent No.: US 7,833,217 B2
(45) Date of Patent: Nov. 16, 2010

(54) FLOATING SPINAL CANNULA AND METHOD OF USE

(75) Inventor: Nicholas M. Boulis, DeCatur, GA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 12/496,400

(22) Filed: Jul. 1, 2009

(65) Prior Publication Data

US 2010/0004625 A1    Jan. 7, 2010

Related U.S. Application Data

(60) Provisional application No. 61/078,004, filed on Jul. 3, 2008.

(51) Int. Cl.
*A61M 25/00* (2006.01)
(52) U.S. Cl. .................. 604/523; 604/240; 604/533
(58) Field of Classification Search ............ 604/523, 604/240, 533, 164.01
See application file for complete search history.

(56) References Cited

U.S. PATENT DOCUMENTS

| 4,676,783 | A | * | 6/1987 | Jagger et al. ............ 604/171 |
| 5,161,542 | A | | 11/1992 | Palestrant |
| 7,014,608 | B2 | | 3/2006 | Larson et al. |
| 7,107,091 | B2 | | 9/2006 | Jutras et al. |
| 2003/0187351 | A1 | | 10/2003 | Franck et al. |
| 2005/0085790 | A1 | | 4/2005 | Guest et al. |
| 2005/0090899 | A1 | | 4/2005 | DiPoto |
| 2008/0154262 | A1 | | 6/2008 | Brundobler et al. |

FOREIGN PATENT DOCUMENTS

| EP | 0 583 049 A1 | 2/1994 |
| WO | WO-96/00044 A1 | 1/1996 |

* cited by examiner

*Primary Examiner*—Kevin C Sirmons
*Assistant Examiner*—Deanna K Hall
(74) *Attorney, Agent, or Firm*—Tarolli, Sundheim, Covell & Tummino LLP

(57) ABSTRACT

A spinal cannula for delivering a therapeutic agent to a spinal cord target includes proximal and distal end portions, a middle portion, and a deployable cannula member having distal and proximal end portions and a first lumen extending between the end portions. The spinal cannula includes a fluid delivery line operably connected to the proximal end portion of the deployable cannula member, and a fluid delivery line including a second lumen in fluid communication with the first lumen. The spinal cannula includes a support cannula proximally located from the deployable cannula member and securely connected to a portion of the fluid delivery line. Additionally, the spinal cannula includes a delivery cannula having distal and proximal end portions and a third lumen extending between the end portions for receiving the support cannula. The proximal end portion includes a locking mechanism for releasably engaging the proximal end portion of the support cannula.

10 Claims, 9 Drawing Sheets

FLOATING SPINAL CANNULA AND METHOD OF USE

RELATED APPLICATION

This application claims priority from U.S. Provisional Patent Application Ser. No. 61/078,004, filed Jul. 3, 2008, the subject matter of which is incorporated hereby incorporated by reference in its entirety.

TECHNICAL FIELD

The present invention relates generally to an apparatus and method for delivering a therapeutic agent to a spinal cord target, and more particularly to a floating spinal cannula and related method for delivering a therapeutic agent to the spinal cord parenchyma.

BACKGROUND OF THE INVENTION

Delivery of therapeutic agents to the spinal cord, such as sustained release preparations of small molecules or peptides, vectors for gene therapy, or cellular transplants to the spinal cord require injection of the spinal cord parenchyma. Penetration of the spinal cord and deployment of a cannula over the time required for injection poses the risk of sheering the axonal tracts of the spinal cord. To avoid this risk, the cannula can be fixed with respect to the spine of the patient to prevent the cannula from shifting during injection. The spinal cord moves with respiration and cardiac rhythm, however, and these movements pose a further risk to the spinal cord during prolonged injection.

SUMMARY OF THE INVENTION

According to one aspect of the present invention, a spinal cannula for delivering a therapeutic agent to a spinal cord target includes proximal and distal end portions. The spinal cannula further comprises a deployable cannula member having a distal end portion, a proximal end portion, a middle portion extending between the distal and proximal end portions, and a first lumen extending between the distal and proximal end portions. The spinal cannula includes a fluid delivery line operably connected to the proximal end portion of the deployable cannula member. The fluid delivery line includes a second lumen in fluid communication with the first lumen of the deployable cannula member. The spinal cannula also includes a support cannula proximally located from the deployable cannula member and being securely connected to a portion of the fluid delivery line. Additionally, the spinal cannula includes a delivery cannula having a distal end portion, a proximal end portion, and a third lumen extending between the distal and proximal end portions for receiving the support cannula. The proximal end portion of the delivery cannula includes a locking mechanism for releasably engaging the proximal end portion of the support cannula.

According to another aspect of the present invention, a method is provided for delivering a therapeutic agent to a spinal cord target. One step of the method includes providing a spinal cannula comprising a deployable cannula member having a distal end portion, a proximal end portion, and a first lumen extending between the end portions, a fluid delivery line operably connected to the proximal end portion of the deployable cannula member and including a second lumen in fluid communication with the first lumen of the deployable cannula member, a support cannula proximally located from the deployable cannula member and securely connected to a portion of the fluid delivery line, and a delivery cannula having a distal end portion, a proximal end portion, and a third lumen extending between the end portions for receiving the support cannula, the proximal end portion of the delivery cannula including a locking mechanism for engaging the proximal end portion of the support cannula. Next, the locking mechanism of the delivery cannula engages the proximal end portion of the support cannula so that the spinal cannula obtains a rigid configuration. The distal end portion of the deployable cannula member is then implanted at the spinal cord target, and the locking mechanism of the delivery cannula is disengaged to release the delivery cannula from the deployable cannula member. Next, the delivery cannula is moved in a proximal direction over the support cannula so that the deployable cannula member is fluidly suspended at the spinal cord target. A therapeutic agent is then infused into the fluid delivery line so that the therapeutic agent is delivered to the spinal cord target.

According to another aspect of the present invention, a spinal cannula is provided for delivering a therapeutic agent to a spinal cord target. The spinal cannula has a distal end portion and a proximal end portion. The spinal cannula comprises a deployable cannula member, a fluid delivery line, a support cannula, and a delivery cannula. The deployable cannula member comprises a needle having a distal end and a proximal end, a hub member having a distal end and a proximal end, a disc-shaped fixing member having oppositely disposed distal and proximal surfaces, and a first lumen extending between the needle and the hub member. The proximal end of the needle is integrally formed with the distal surface of the fixing member, and the distal end of the hub member is integrally formed with the proximal surface of the fixing member. The fluid delivery line is operably connected to the proximal end of the hub member. The fluid delivery line includes a second lumen in fluid communication with the first lumen. The support cannula is proximally located from the deployable cannula member and is securely connected to a portion of the fluid delivery line. The delivery cannula has a distal end portion, a proximal end portion, and a third lumen extending between the distal and proximal end portions for receiving the support cannula. The proximal end portion includes a locking mechanism for releasably engaging the proximal end portion of the support cannula.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1A:
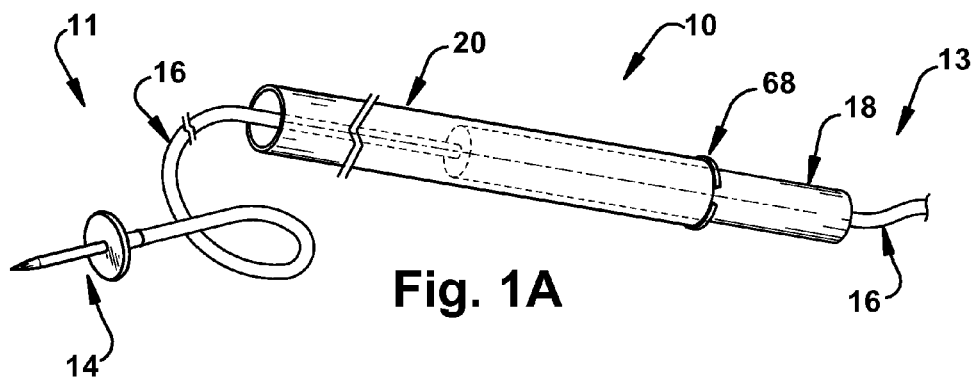
FIG. 1A is a perspective view of a spinal cannula having a flexible configuration and being constructed in accordance with the present invention.
Figure 1B:
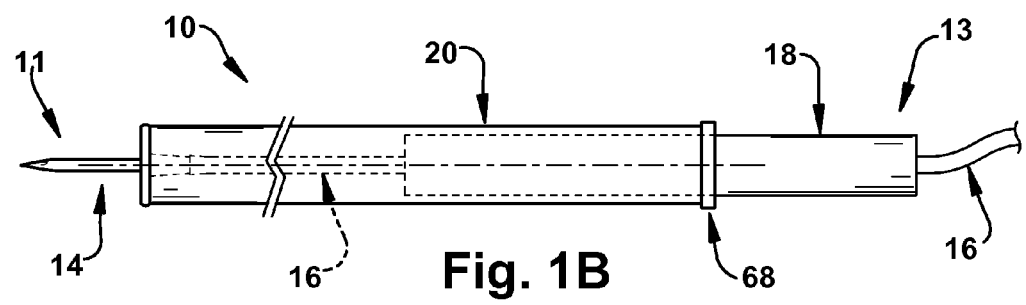
FIG. 1B is a perspective view showing the spinal cannula in FIG. 1A having a rigid configuration.

The present invention relates generally to an apparatus and method for delivering a therapeutic agent to a spinal cord target, and more particularly to a floating spinal cannula and related method for delivering a therapeutic agent to the spinal cord parenchyma. As representative of the present invention, FIG. 1A illustrates a spinal cannula 10 for delivering a therapeutic agent to a spinal cord target. As described in more detail below, the spinal cannula 10 can have a rigid configuration (FIG. 1B) to facilitate placement of the spinal cannula, and a flexible configuration (FIG. 1A) that allows a portion of the spinal cannula to float or move with the spinal cord 12 (FIG. 6) and thereby prevent or mitigate damage to the spinal cord caused by cardiac or respiratory variations.

Figure 2A:
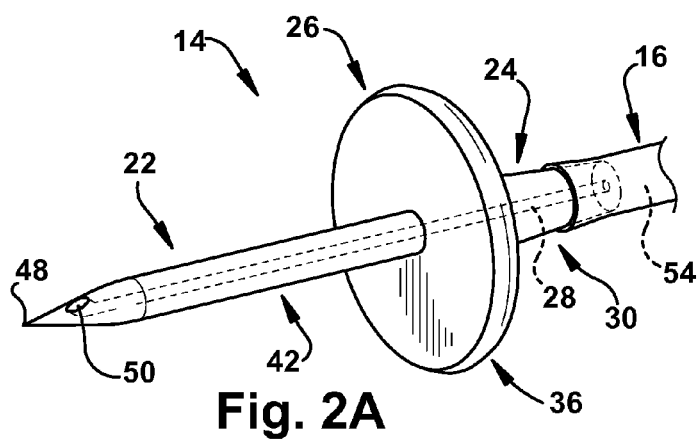
FIG. 2A is a perspective view showing a deployable cannula member of the spinal cannula in FIGS. 1A-B.
Figure 2B:
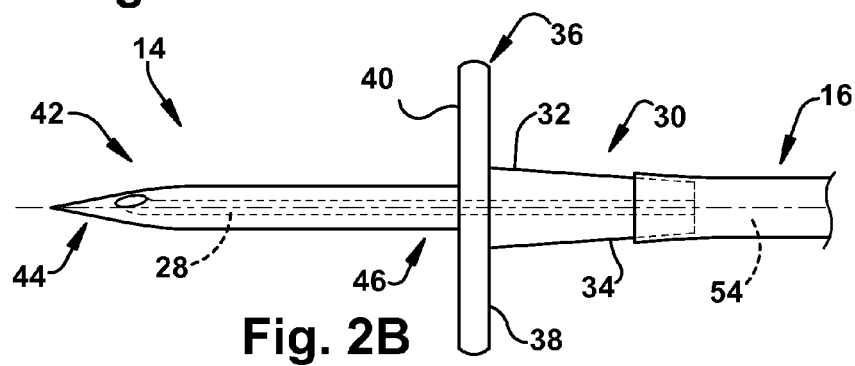
FIG. 2B is a side view of the deployable cannula member in FIG. 2A.

As shown in FIG. 1A, the spinal cannula 10 includes a distal end portion 11 and a proximal end portion 13, and comprises a deployable cannula member 14, a fluid delivery line 16, a support cannula 18, and a delivery cannula 20. The deployable cannula member 14 comprises a distal end portion 22, a proximal end portion 24, and a middle portion 26 extending between the distal and proximal end portions. As illustrated in FIGS. 2A-B, the deployable cannula member 14 includes a first lumen 28 extending between the distal and proximal end portions 22 and 24. Depending upon the particular spinal cord target, the deployable cannula member 14 can have any appropriate size and shape.

The proximal end portion 24 of the deployable cannula member 14 comprises a hub member 30 having a distal end 32 and a proximal end 34. The proximal end 34 of the hub member 30 is adapted for connection to the fluid delivery line 16, and the distal end 32 is integrally formed with the middle portion 26 of the deployable cannula member 14. The hub member 30 has a tapered configuration to facilitate placement of the fluid delivery line 16 over the proximal end 34. The hub member 30 can have a rigid or semi-rigid configuration and can be made of any one or combination of biocompatible materials, such as stainless steel, titanium, polyvinyl chloride (PVC), polymethylmethacrylate (PMMA), and the like.

The middle portion 26 of the deployable cannula member 14 includes a fixing member 36 having oppositely disposed proximal and distal surfaces 38 and 40. As described in more detail below, the fixing member 36 facilitates placement of the distal end portion 22 of the deployable cannula member 14 to a pre-determined depth at the spinal cord target. The proximal surface 38 of the fixing member 36 is integrally formed with the distal end 32 of the hub member 30, and the distal surface 40 is integrally formed with the distal end portion 22 of the deployable cannula member 14. As shown in FIGS. 2A-B, the fixing member 36 has a flattened, disc-like shape. It will be appreciated, however, that the fixing member 36 can have any shape and size to facilitate placement of the deployable cannula member 14 at a pre-determined depth. The fixing member 36 can be made of any one or combination of biocompatible materials, such as stainless steel, titanium, PVC, PMMA, and the like.

The distal end portion 22 of the deployable cannula member 14 comprises a needle 42 having a distal end 44 and a proximal end 46. The proximal end 46 of the needle 42 is integrally formed with the distal surface 40 of the fixing member 36, and the distal end 44 of the needle has a sharpened tip 48 for penetrating tissue. As shown in FIG. 2A, the distal end 44 of the needle 42 also includes a port 50 in fluid communication with the first lumen 28 for delivering a therapeutic agent to the spinal cord target. The proximal and distal ends 46 and 44 of the needle 42 define a length L that can be varied depending on the location (i.e., depth) of the particular spinal cord target. For example, the needle 42 can have a length L of about 1 mm to about 8 mm. For placement at the ventral horn 52 (FIG. 6), for instance, the needle 42 (FIGS. 2A-B) can have a length L of about 5 mm. The gauge of the needle 42 can be varied between 10 g and 33 g, for example, also depending upon the particular spinal cord target. It will be appreciated that the diameter of the fixing member 36 is greater than the diameter of the needle 42 and the hub member 30.

Referring again to FIG. 1A, the spinal cannula 10 also includes a fluid delivery line 16 operably coupled to the proximal end 34 of the hub member 30. The fluid delivery line 16 includes a second lumen 54 in communication with the first lumen 28 of the deployable cannula member 14. The fluid delivery line 16 can be securely fastened to the hub member 30 by applying an adhesive (e.g., epoxy) to the proximal end 34 of the hub member and then advancing the fluid delivery line over the proximal end until the fluid delivery line is securely connected to the hub member. Alternatively, a fluid delivery line 16 having a diameter less than the diameter of the first lumen 28 can be friction fit into the first lumen so that the first lumen and the second lumen 54 are in fluid communication.

The fluid delivery line 16 can comprise any biocompatible, medical grade material, such as TEFLON. Additionally, the fluid delivery line 16 can have a narrow gauge to facilitate flexibility of the spinal cannula 10. The entire fluid delivery line 16 can be made of the same material or, alternatively, different portions of the fluid delivery line can be made of different materials to impart different properties (e.g., flexibility) to the different portions. For example, the portion of the fluid delivery line 16 extending between the deployable cannula member 14 and the support cannula 18 can have a different composition as compared to the portion of the fluid delivery line extending from a proximal end portion 56 (FIGS. 3A-C) of the support cannula so that this portion is more flexible than the rest of the fluid delivery line.

Figure 3A:
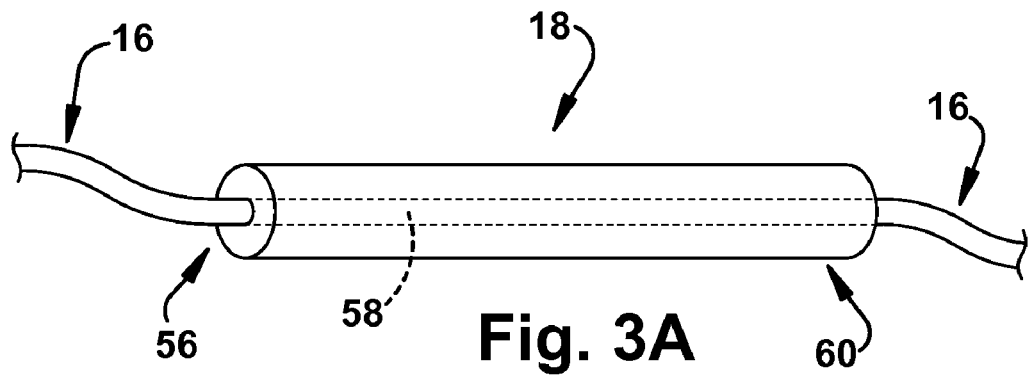
FIG. 3A is a perspective view showing a support cannula of the spinal cannula in FIGS. 1A-B.
Figure 3B:
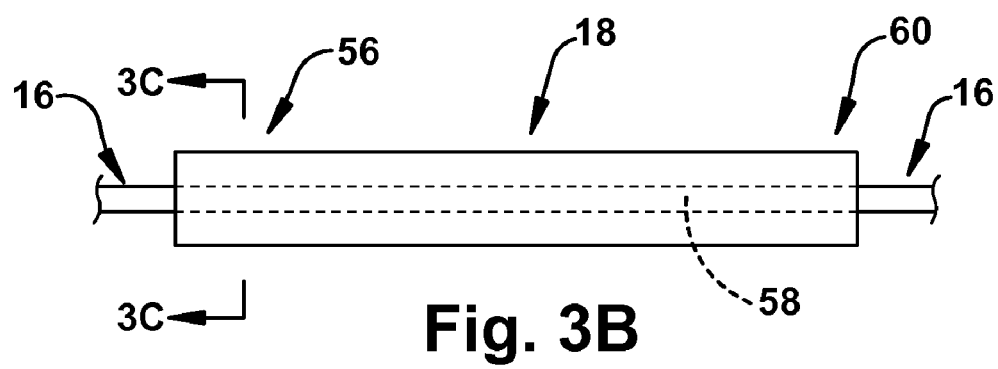
FIG. 3B is a side view of the support cannula in FIG. 3A.
Figure 3C:
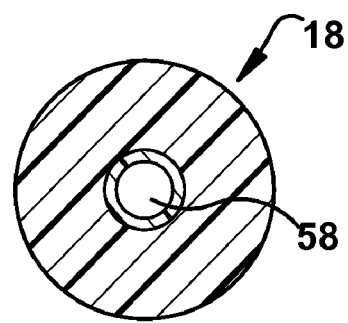
FIG. 3C is a cross-sectional view taken along Line 3C-3C in FIG. 3B.

As shown in FIGS. 3A-C, the spinal cannula 10 additionally includes a support cannula 18 proximally located from the deployable cannula member 14 and securely connected to a portion of the fluid delivery line 16. The support cannula 18 has an elongated, tube-like configuration and includes a passage 58 extending between the proximal end portion 56 and a distal end portion 60. Each of the proximal and distal end portions 56 and 60 are integrally connected with the fluid delivery line 16 so that the passage 58 is in fluid communication with the second lumen 54 of the fluid delivery line. For example, the fluid delivery line 16 can be connected to the proximal and distal end portions 56 and 60 using an adhesive (e.g., epoxy). Alternatively, the fluid delivery line 16 can extend through the passage 58 of the support cannula 18. The support cannula 18 can have a rigid, semi-rigid, or flexible configuration and can be made of any one or combination of biocompatible materials, such as stainless steel, titanium, PVC, PMMA, and the like. As described in more detail below, the support cannula 18 facilitates placement of the deployable cannula member 14 at the spinal cord target.

Referring again to FIG. 1A, the spinal cannula 10 further comprises a delivery cannula 20 having an elongated, tube-like configuration and comprising proximal and distal end portions 62 and 64. The delivery cannula 20 includes a third lumen (not shown) extending between the proximal and distal end portions 62 and 64. As described in more detail below, the third lumen is capable of receiving both the fluid delivery line 16 and the support cannula 18 to facilitate movement of the spinal cannula 10 between the flexible and rigid configurations. The delivery cannula 20 can have a rigid configuration and can be made of any one or combination of biocompatible materials, such as stainless steel, titanium, PVC, PMMA, and the like.

Figure 4A:
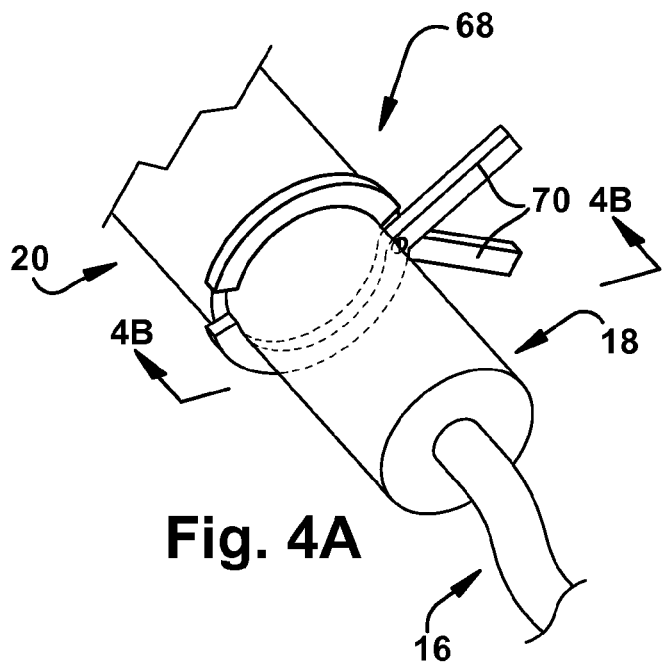
FIG. 4A is a perspective view showing a locking mechanism of the spinal cannula in FIGS. 1A-B.
Figure 4B:
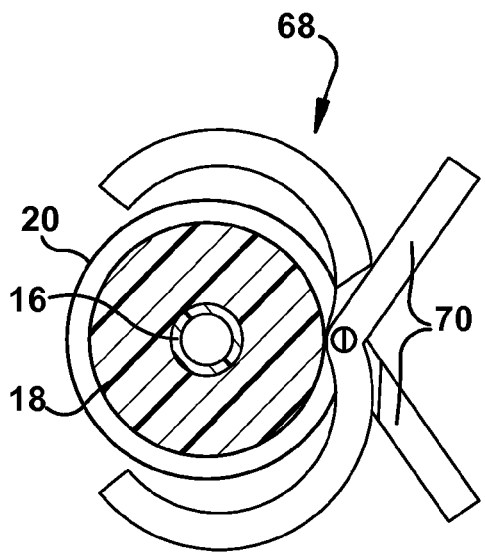
FIG. 4B is a cross-sectional view taken along Line 4B-4B in FIG. 4A showing the locking mechanism engaged with the support cannula.
Figure 4C:
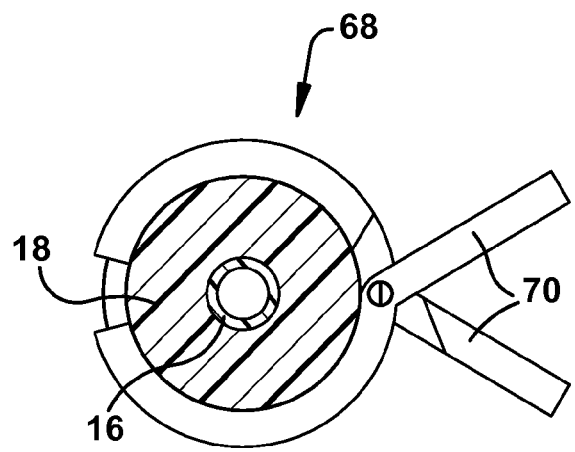
FIG. 4C is a cross-sectional view similar to FIG. 4B showing the locking mechanism disengaged from the support cannula.

The delivery cannula 20 also includes a locking mechanism 68 for selectively engaging the support cannula 18. As shown in FIG. 4A, the locking mechanism 68 has a clip or clamp-like configuration and is operably disposed at the proximal end portion 62 of the delivery cannula 20. The locking mechanism 68 includes opposable jaw members 70, each of which is configured to extend around a portion of the support cannula 18. The jaw members 70 can be manipulated via a spring-loaded mechanism so that the locking mechanism 68 moves between a closed configuration (FIG. 4B) and an open configuration (FIG. 4C). Although the locking mechanism 68 is shown in FIGS. 4A-B as being operably disposed at the proximal end portion 62 of the delivery cannula 20, it should be appreciated that the locking mechanism may be entirely removable from the delivery cannula.

It should also be appreciated that the spinal cannula 10 can include an imaging component (not shown) to facilitate real-time imaging and placement of the spinal cannula. For example, the spinal cannula 10 can include at least one imaging coil disposed on the deployable cannula member 14 to facilitate placement of the spinal cannula using OCT or MR imaging. Additionally, it will be appreciated that the spinal cannula 10 can include at least one electrode (not shown) for delivering or recording electric current to a spinal cord target. For example, an electrode can be operably coupled to the spinal cannula 10 for therapeutic and/or diagnostic (e.g., microelectrode recording) purposes.

Figure 5:
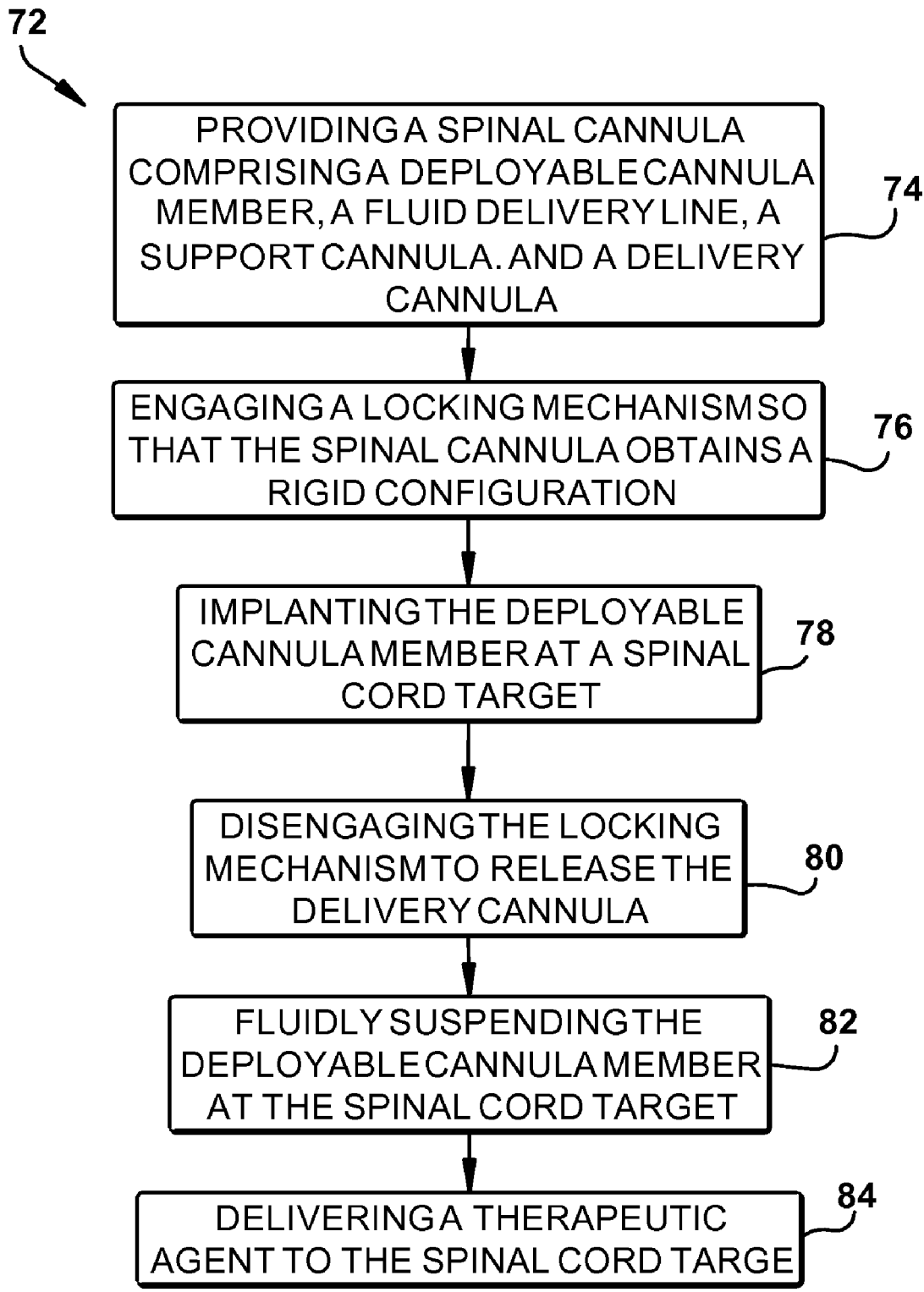
FIG. 5 is a process flow diagram illustrating a method for delivering a therapeutic agent to a spinal cord target in accordance with another aspect of the present invention.
Figure 6:
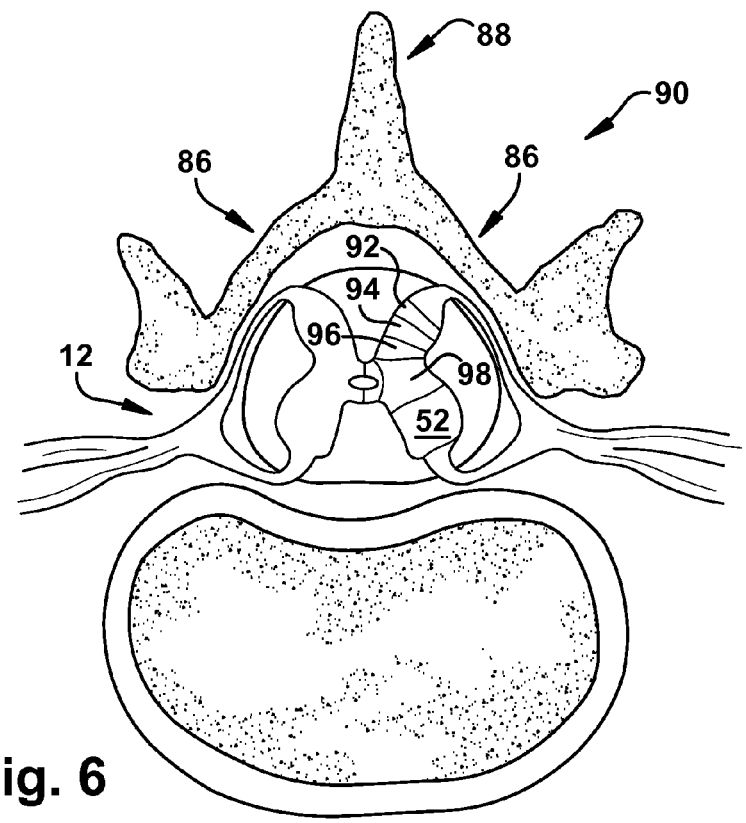
FIG. 6 is a cross-sectional view of a vertebral column showing a vertebral body and the spinal cord.

FIG. 5 is a process flow diagram illustrating another aspect of the present invention. In FIG. 5, a method 72 is provided for delivering a therapeutic agent to a spinal cord target, such as a ventral horn 52 (also referred to as the anterior gray horn) (FIG. 6). Although the method 72 is described below in terms of delivering a therapeutic agent to the ventral horn 52, it will be appreciated that the spinal cord target can comprise any portion of the spinal cord parenchyma and the structures associated therewith. For example, the spinal cord target can include, but is not limited to, a portion of the posterior white column, a portion of the lateral white column, a portion of the anterior white column, a portion of the posterior gray horn, a portion of the lateral gray horn, a portion of the posterior gray commissure, a portion of the anterior gray commissure, a portion of the anterior white commissure, the central canal, and combinations thereof.

The spinal cord target is selected based on a number of anatomical and physiological factors, including the accessibility of the spinal cord target and the type of disease or disorder being treated. Where a subject is suffering from a motor neuron disease, for example, the spinal cord target can comprise the ventral horn 52 as the ventral horn includes motor nuclei of the somatic nervous system. A variety of other nervous system diseases or disorders can be treated according to the present method, including, but not limited to, neuropathies, injuries of the spinal cord 12, demyelinating diseases, pain, spasticity, and infiltrating tumors of the spinal cord.

The type and amount of therapeutic agent delivered to the spinal cord target will depend on the type and severity of the nervous system disease being treated. As used herein, the term "therapeutic agent" can refer to any substance that, when administered in a therapeutically effective amount to a subject suffering from a nervous system disease, has a therapeutic beneficial effect on the health and well-being of the subject. A therapeutic beneficial effect on the health and well-being of a subject includes, but it not limited to: (1) curing the disease; (2) slowing the progress of the disease; (3) causing the disease to retrogress; or (4) alleviating one or more symptoms of the disease.

The term "therapeutic agent" can also include any substance that, when administered to a subject known or suspected of being particularly susceptible to a disease, has a prophylactic beneficial effect on the health and well-being of the subject. A prophylactic beneficial effect on the health and well-being of a subject includes, but is not limited to: (1) preventing or delaying on-set of the disease in the first place; (2) maintaining a disease at a retrogressed level once such level has been achieved by a therapeutically effective amount of a substance (which may be the same as or different from the substance used in a prophylactically effective amount); or (3) preventing or delaying recurrence of the disease after a course of treatment with a therapeutically effective amount of a substance (which may be the same as or different from the substance used in a prophylactically effective amount).

Non-limiting examples of therapeutic agents that can be delivered to the spinal cord target can include small molecules (i.e., organic compounds, whether naturally-occurring or artificially created that have relatively low molecular weight and that do not include proteins, polypeptides, or nucleic acids), polypeptides, polynucleotides, viral vectors, and cell transplants, such as immune cell transplants (e.g., macrophage and T cells) and fetal or adult progenitor cells, i.e., any totipotent stem cell, pluripotent stem cell, and multipotent stem cell, as well as any of their lineage descendant cells that have the capacity to differentiate into a specific type of cell. Therapeutic agents can be delivered to the spinal cord target to affect nervous tissue function immediately or, alternatively, delivered as part of a controlled or sustained release for calculated release into the nervous tissue comprising the spinal cord target.

Where a subject is afflicted with a motor neuron disease, for example, a therapeutically effective amount of fetal progenitor cells can be delivered to the ventral horn 52 of the subject according to the method 72 of the present invention. As used herein, the term "therapeutically effective amount" can refer to that amount of a therapeutic agent that relieves to some extent one or more symptoms of a nervous system disease or disorder, or returns to normal, either partially or completely, one or more physiological or biochemical parameters associated with or causative of the nervous system disease or disorder.

As shown in FIG. 5, one step of the method includes providing a spinal cannula 10 at 74. Prior to providing the spinal cannula 10, however, the spinal cord target is assessed using any one or combination of known imaging modalities (e.g., CT, MRI, etc.) to evaluate the anatomy at (and surrounding) the spinal cord target. For example, the dimensions of the dorsal lamina 86 and the spinous process 88, as well as the thickness of the lateral white column surrounding the ventral horn 52 can be determined using CT and/or MRI. Once the anatomical dimensions of the spinal cord target have been determined, an appropriately-sized spinal cannula 10 is selected. For example, a deployable cannula member 14 can be selected that has a needle 42 with a length L that corresponds to the distance between the ventral horn 52 and the outer portion of the spinal cord 12.

Figure 7:
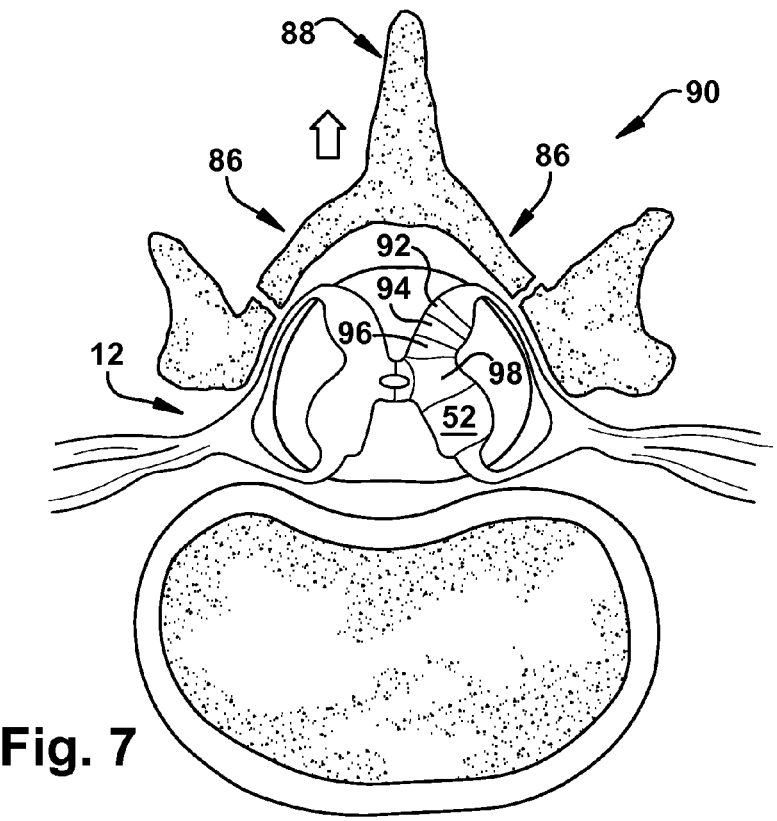
FIG. 7 is a cross-sectional view of the vertebral body in FIG. 6 undergoing a dorsal laminectomy.

To access the ventral horn 52, a dorsal laminectomy is performed using a minimally invasive or open surgical procedure. Using a minimally invasive approach, for example, the laminectomy is performed by making a small skin incision (not shown) over the vertebra 90 and then pushing aside the back muscles (not shown) to expose the dorsal lamina 86. A bone cutting tool (not shown) is then used to remove the lamina 86 and the spinous process 88 as shown in FIG. 7. Removal of the lamina 86 and the spinous process 88 exposes the dorsal surface of the spinal cord 12. It should be appreciated that other approaches, such as a percutaneous approach may be used to deliver the spinal cannula 10 to a spinal cord target.

If it has not been done so already, the spinal cannula 10 is next placed in the rigid configuration at 76. To place the spinal cannula 10 in the rigid configuration, the locking mechanism 68 is manipulated so that the jaw members 70 obtain the open configuration. Next, the delivery cannula 20 is moved in a distal direction relative to the support cannula 18 until the distal end portion 64 of the delivery cannula engages the proximal surface 38 of the fixing member 36. Once the distal end portion 64 of the delivery cannula 20 engages the proximal surface 38 of the fixing member 36, the locking mechanism 68 is manipulated so that the jaw members 70 obtain the closed position and securely engage the support cannula 18 (FIG. 4B).

Figure 8:
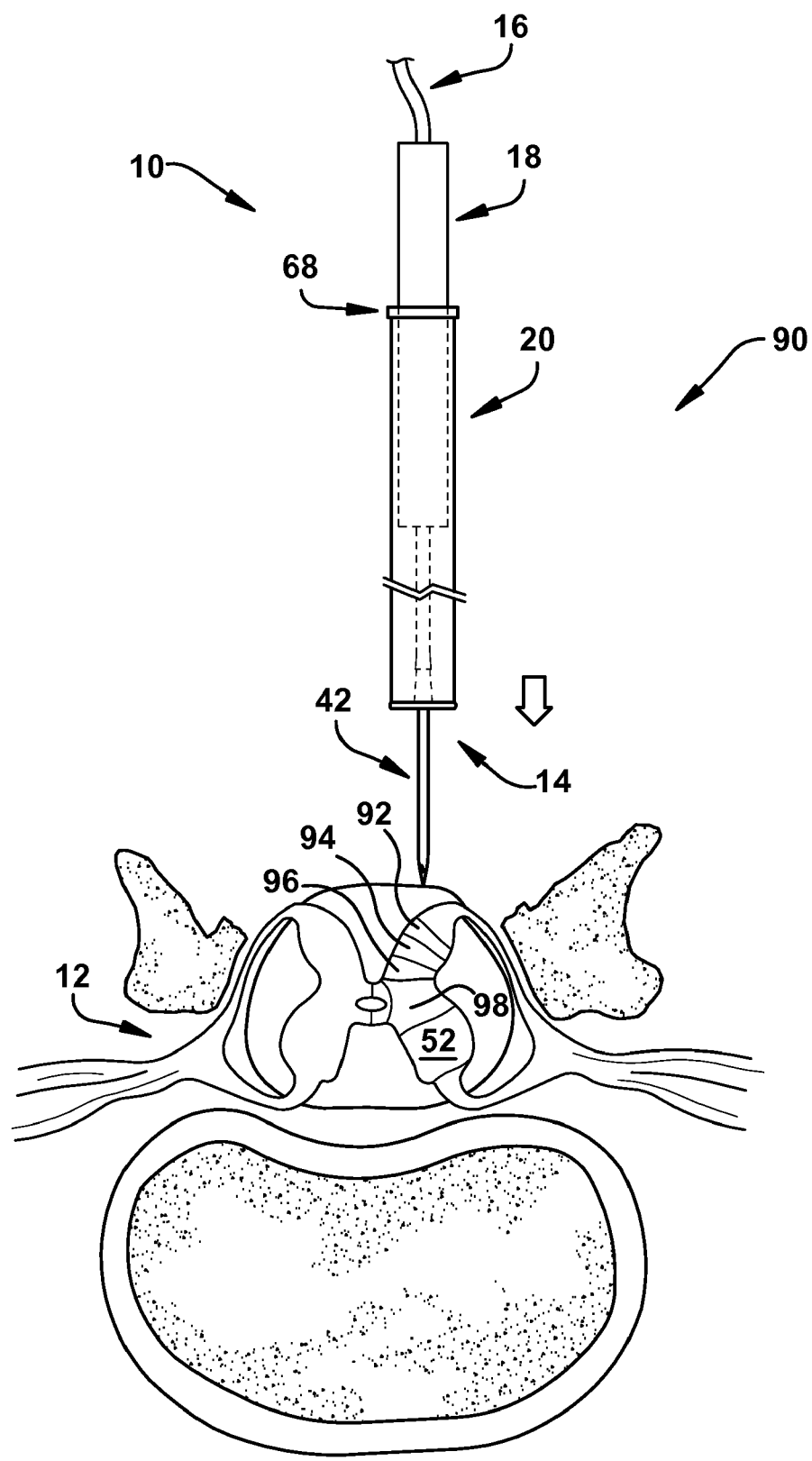
FIG. 8 is a cross-sectional view of the vertebral body in FIG. 7 showing the spinal cannula in FIG. 1B positioned substantially perpendicular to the spinal cord.
Figure 9:
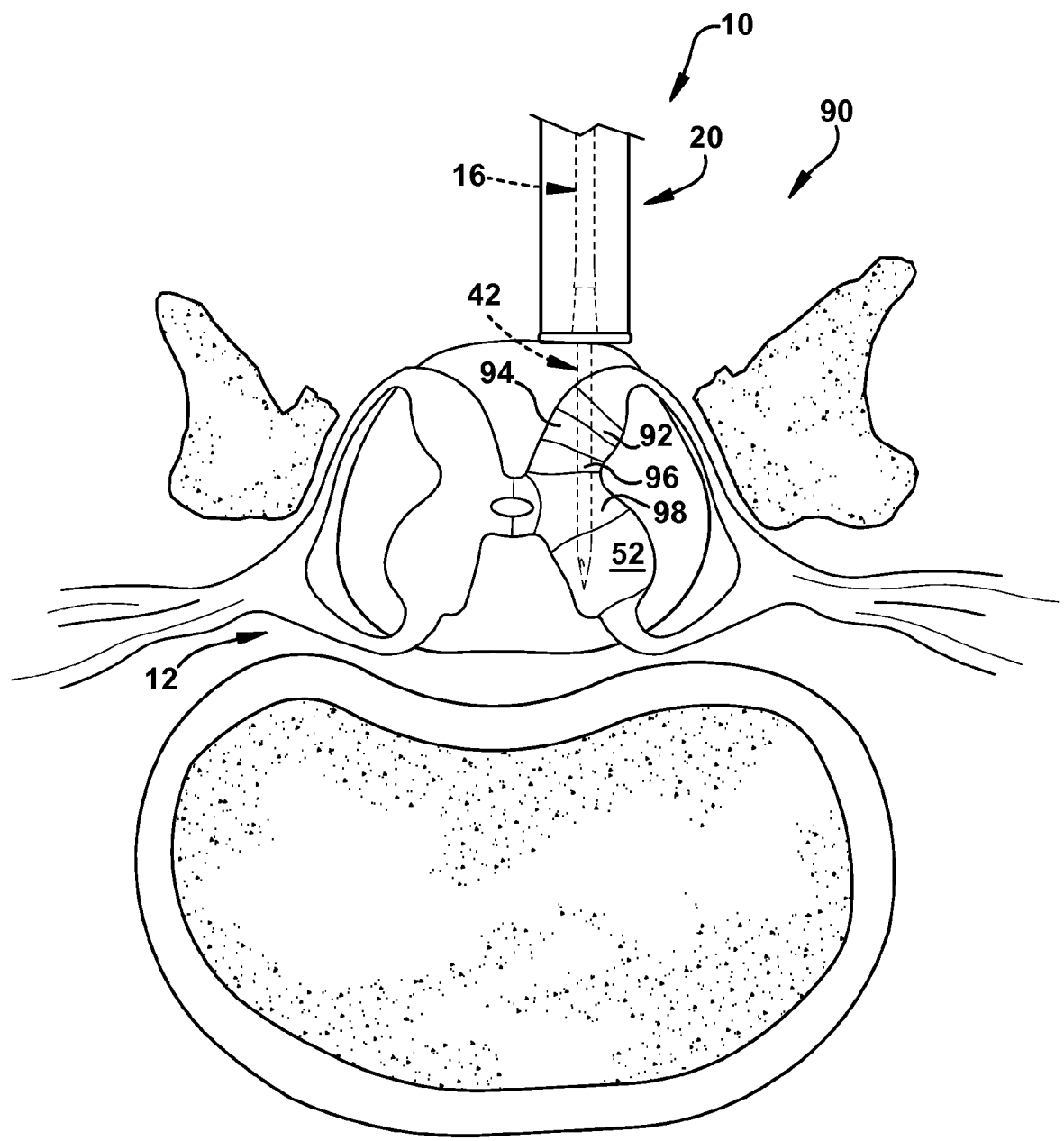
FIG. 9 is an exploded cross-sectional view of the vertebral body in FIG. 8 showing the deployable cannula member extending into the ventral horn.

After placing the spinal cannula 10 in the rigid configuration, the spinal cannula is positioned substantially perpendicular to the spinal cord 12 as shown in FIG. 8. At 78, the distal end portion 11 of the spinal cannula 10 is then implanted at the spinal cord target. To implant the distal end portion 11 at the spinal cord target, the dura mater (not shown) and the pia mater are opened to visualize the vasculature on the spinal cord 12, such as the dorsal rootlets and the needle 42 then advanced until the distal surface 40 of the fixing member 36 contacts the outer dorsal surface of spinal cord (FIG. 9). It should be appreciated, however, that the distal end portion 11 can alternatively be urged through dura mater and into the subarachnoid space (not shown in detail) until the distal end 44 of the needle 42 contacts the pia mater, followed by advancement of the needle through the pia mater. With the distal surface 40 of the fixing member 36 in contact with the outer dorsal surface of the spinal cord 12, the distal end 44 of the needle 42 extends through the marginal zone 92, the substantia gelatinosa 94, the body of the dorsal horn 96, and the intermediate horn 98 of the spinal cord into a portion of the ventral horn 52.

Figure 10:
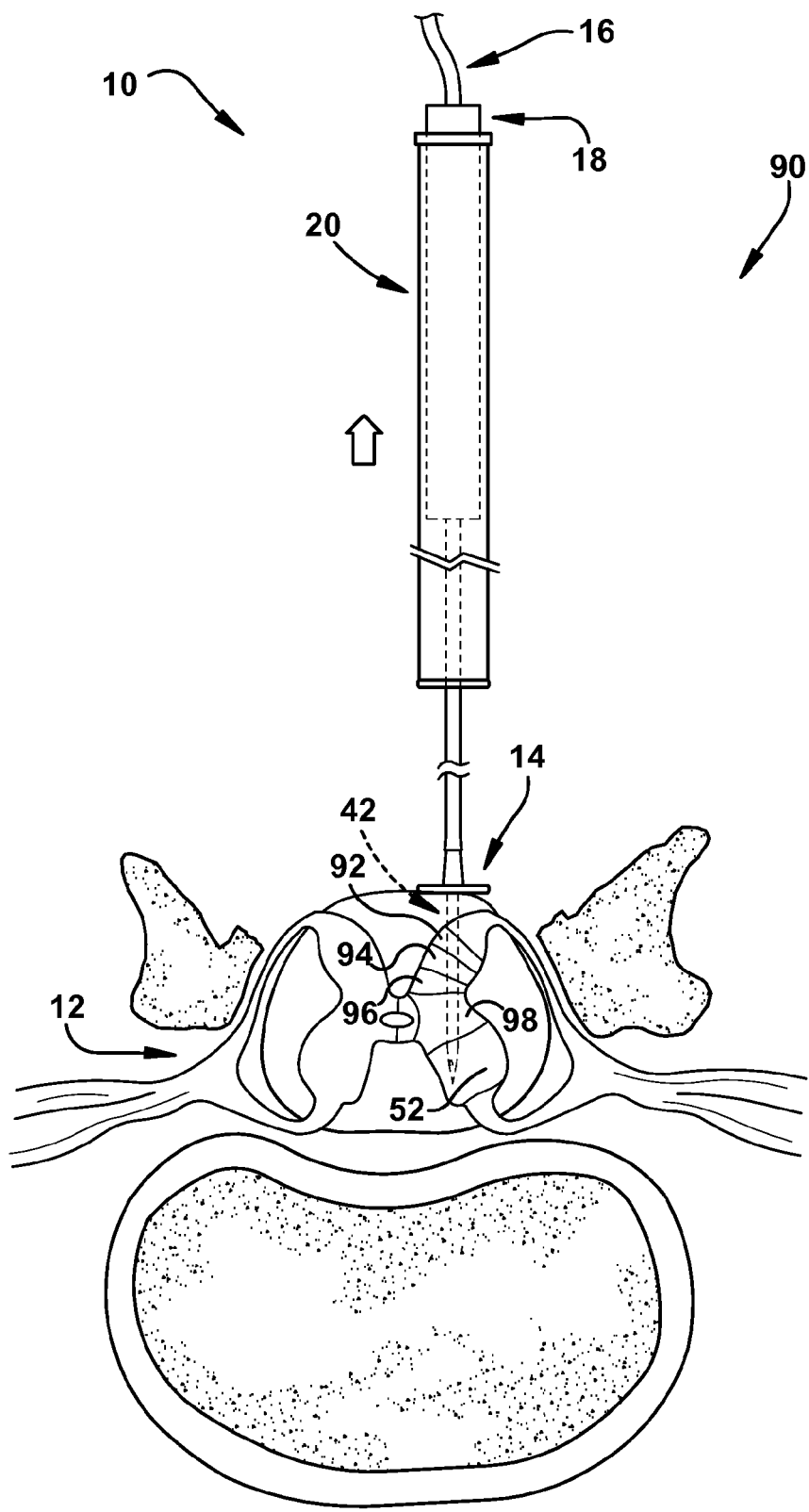
FIG. 10 is an cross-sectional view of the vertebral body in FIG. 8 showing deployment of the spinal cannula.
Figure 11:
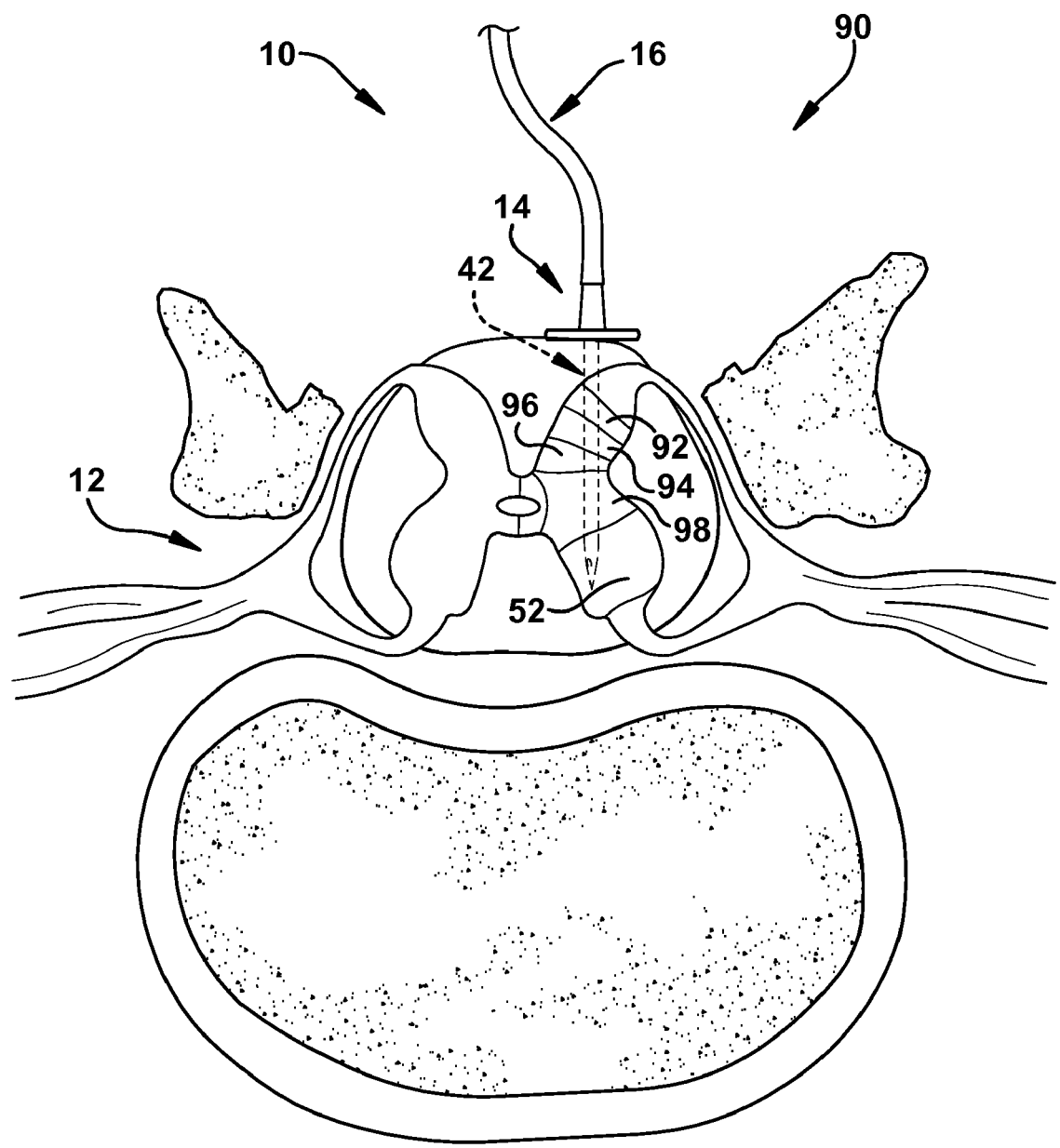
FIG. 11 is a cross-sectional view of the vertebral body in FIG. 10 showing the spinal cannula deployed at the spinal cord target.

At 80, the locking mechanism 68 is placed in the open configuration so that the jaw members are disengaged from the support cannula 18. After placing the locking mechanism 68 in the open configuration, the delivery cannula 20 is moved in a proximal direction relative to the support cannula 18 (at 82) so that the distal end portion 64 of the delivery cannula is no longer in contact with the proximal surface 38 of the fixing member 36 (FIG. 10). As shown in FIG. 11, the delivery cannula 20 is then sufficiently withdrawn to expose a portion of the fluid delivery line 16. Depending upon the anatomy of the subject, for example, the length of the exposed portion of the fluid delivery line 16 can be varied as needed. For example, the exposed fluid delivery line 16 can be about 2 cm to about 3 cm in length. With the deployable cannula member 14 securely implanted at the spinal cord target, the deployable cannula member can move freely in response to variations in cardiac rhythm and respiration without being dislodged from and/or damage the spinal cord 12.

Once the deployable cannula member 14 is securely positioned at the spinal cord target, a therapeutically effective amount of the therapeutic agent is delivered to the spinal cord target at 84. For example, a therapeutically effective amount of fetal progenitor cells can be infused into the fluid delivery line 116 via a therapeutic agent delivery device (e.g., a syringe or microdrive pump) at an appropriate rate and concentration. One example of such a therapeutic delivery device can include the spinal delivery platform disclosed in U.S. patent application Ser. No. 12/418,170, filed Apr. 3, 2009 and entitled "Spinal Platform and Method for Delivering a Therapeutic Agent to a Spinal Cord Target", the entirety of which is hereby incorporated by reference. The fetal progenitor cells are then delivered to the ventral horn 52 to mitigate or prevent symptoms associated with the motor neuron disease. The floating, deployable cannula member 14 facilitates a slower infusion of the therapeutic agent without damage secondary to a mass of fluid and pressure. The slower infusion rate, in turn, mitigates reflux of the therapeutic agent and promotes atraumatic dispersion of the therapeutic agent into the tissue surrounding the spinal cord target.

Once the deployable cannula member 14 is implanted, the delivery cannula 20 is locked at a desired point over the support cannula 18. To stabilize the spinal cannula 10 during infusion of the therapeutic agent, the delivery cannula 20 can be securely attached to a delivery platform (not shown) or other stationary device to prevent the spinal cannula from being bumped or moved. Doing so may prevent the deployable cannula member 14 from being accidentally pulled out of the spinal cord 12. For example, securing the spinal cannula 10 may prevent pull out of the deployable cannula member 14 if a person were to accidentally tug or pull on the fluid delivery line 16 that extends between the deployable cannula member and the fluid delivery device.

From the above description of the invention, those skilled in the art will perceive improvements, changes and modifications. Such improvements, changes, and modifications are within the skill of the art and are intended to be covered by the appended claims.

Having described the invention, the following is claimed:

1. A spinal cannula for delivering a therapeutic agent to a spinal cord target, said spinal cannula having a distal end portion and a proximal end portion, said spinal cannula comprising:

a deployable cannula member having a distal end portion, a proximal end portion, a middle portion extending between said distal and proximal end portions, and a first lumen extending between said distal and proximal end portions;

a fluid delivery line operably connected to said proximal end portion of said deployable cannula member, said fluid delivery line including a second lumen in fluid communication with said first lumen of said deployable cannula member;

a support cannula proximally located from said deployable cannula member and securely connected to a portion of said fluid delivery line; and a delivery cannula having a distal end portion, a proximal end portion, and a third lumen extending between said distal and proximal end portions for receiving said support cannula, said proximal end portion including a locking mechanism for releasably engaging said proximal end portion of said support cannula;

wherein said middle portion of said deployable cannula member comprises a flattened, disc-like fixing member including oppositely disposed proximal and distal surfaces;

wherein said distal end portion of said deployable cannula member further comprises a needle having a distal end and a proximal end, said proximal end being integrally formed with said distal surface of said fixing member.

2. The spinal cannula of claim 1, wherein said proximal end portion of said deployable cannula member further includes a hub member having a proximal end and a distal end, said distal end being integrally formed with said proximal surface of said fixing member.

3. The spinal cannula of claim 1, wherein said spinal cannula has a rigid configuration when said locking mechanism is engaged with said proximal end portion of said support cannula.

4. The spinal cannula of claim 3, wherein said proximal surface of said fixing member is in contact with said proximal end portion of said delivery cannula in the rigid configuration.

5. The spinal cannula of claim 1, wherein said spinal cannula has a flexible configuration when said locking mechanism is disengaged from said proximal end portion of said support cannula.

6. The spinal cannula of claim 5, wherein said fixing member is separated from said delivery cannula in the flexible configuration.

7. The spinal cannula of claim of claim 2, wherein said fixing member has a diameter greater than the diameter of said needle and the diameter of said hub member.

8. The spinal cannula of claim 1, wherein said locking mechanism is integrally formed with said proximal end portion of said delivery cannula.

9. A spinal cannula for delivering a therapeutic agent to a spinal cord target, said spinal cannula having a distal end portion and a proximal end portion, said spinal cannula comprising:

a deployable cannula member comprising a needle having a distal end and a proximal end, a hub member having a distal end and a proximal end, a disc-shaped fixing member having oppositely disposed distal and proximal surfaces, and a first lumen extending between said needle and said hub member, said proximal end of said needle being integrally formed with said distal surface of said fixing member and said distal end of said hub member being integrally formed with said proximal surface of said fixing member;

a fluid delivery line operably connected to said proximal end of said hub member, said fluid delivery line including a second lumen in fluid communication with said first lumen;

a support cannula proximally located from said deployable cannula member and securely connected to a portion of said fluid delivery line; and a delivery cannula having a distal end portion, a proximal end portion, and a third lumen extending between said distal and proximal end portions for receiving said support cannula, said proximal end portion including a locking mechanism for releasably engaging said proximal end portion of said support cannula.

10. The spinal cannula of claim 9, wherein said fluid delivery line is directly connected to said proximal end of said hub member.

* * * * *